US008399506B2

(12) United States Patent
Kempen

(10) Patent No.: US 8,399,506 B2
(45) Date of Patent: Mar. 19, 2013

(54) COMBINATIONS OF 4 BROMO-2-(4-CHLOROPHENYL)-5-(TRIFLUOROMETHYL)-1H-PYRROLE-3-CARBONITRILE AND OXIDIZING AGENTS

(75) Inventor: Tony Mathilde Jozef Kempen, Kapellen (BE)

(73) Assignee: Janssen Pharmaceutica, NV (BE)

( * ) Notice: Subject to any disclaimer, the term of this patent is extended or adjusted under 35 U.S.C. 154(b) by 488 days.

(21) Appl. No.: 12/376,680

(22) PCT Filed: Aug. 6, 2007

(86) PCT No.: PCT/EP2007/058132
§ 371 (c)(1),
(2), (4) Date: Feb. 6, 2009

(87) PCT Pub. No.: WO2008/017656
PCT Pub. Date: Feb. 14, 2008

(65) Prior Publication Data
US 2010/0178357 A1 Jul. 15, 2010

(30) Foreign Application Priority Data
Aug. 7, 2006 (EP) .................................. 06118511

(51) Int. Cl.
A01N 43/36 (2006.01)
A01N 39/00 (2006.01)
A01N 59/00 (2006.01)
A01N 59/02 (2006.01)
A01N 59/08 (2006.01)
A01N 59/16 (2006.01)
A01N 55/02 (2006.01)

(52) U.S. Cl. ........ 514/427; 424/613; 424/616; 424/646; 424/661; 424/665; 424/709; 424/711; 424/713; 504/151; 504/152; 504/156

(58) Field of Classification Search .................. 514/427; 424/613, 616, 646, 661, 665, 709, 711, 713; 504/151, 152, 156
See application file for complete search history.

(56) References Cited

U.S. PATENT DOCUMENTS

| | | | |
|---|---|---|---|
| 6,069,189 A | 5/2000 | Kramer et al. | |
| 6,291,549 B1 | 9/2001 | Mechtel et al. | |
| 2006/0089352 A1 | 4/2006 | Bruns et al. | |
| 2008/0090938 A1 | 4/2008 | Quaiser et al. | |
| 2008/0175812 A1 | 7/2008 | Seabrook et al. | |
| 2009/0017135 A1 | 1/2009 | Kempen | |
| 2009/0093443 A1 | 4/2009 | Kempen | |
| 2011/0160258 A1 | 6/2011 | Van Der Flaas et al. | |
| 2011/0160275 A1 | 6/2011 | Van Der Flaas et al. | |
| 2011/0237632 A1 | 9/2011 | Kempen | |

FOREIGN PATENT DOCUMENTS

| | | |
|---|---|---|
| EP | 0312723 B1 | 4/1989 |
| EP | 0746979 A1 | 12/1996 |
| EP | 0831134 | 3/1998 |
| EP | 1769680 B1 | 4/2007 |
| JP | 2001-502732 A | 2/2001 |
| WO | 95/05739 A1 | 3/1995 |
| WO | 95/06043 A1 | 3/1995 |
| WO | 97/42823 A1 | 11/1997 |
| WO | 98/12269 A1 | 3/1998 |
| WO | 98/17732 A1 | 4/1998 |
| WO | 01/95718 A1 | 12/2001 |
| WO | 03/039256 A | 5/2003 |
| WO | WO 03/039256 A1 * | 5/2003 |
| WO | 2005/025313 A1 | 3/2005 |
| WO | 2005/075581 | 8/2005 |
| WO | 2006/080890 A1 | 8/2006 |
| WO | WO 2007/088172 A2 * | 8/2007 |
| WO | WO 2007/116051 A1 * | 10/2007 |
| WO | 2012/001027 | 1/2012 |

OTHER PUBLICATIONS

Raymond A. Cloyd (2011). Pesticide Mixtures, Pesticides—Formulations, Effects, Fate, Margarita Stoytcheva (Ed.), p. 69-80, ISBN: 978-953-307-532-7, InTech, Available from: http://www.intechopen.com/articles/show/title/pesticide-mixtures.*
International Search Report and Written Opinion, PCT/EP2007/050927, date of mailing Nov. 1, 2007.
PCT counterpart to U.S. Appl. No. 10/494,751, International Search Report, PCT/EP2002/12376, date of mailing Mar. 12, 2003.
PCT counterpart to U.S. Appl. No. 12/296,353, International Search Report and Written Opinion, PCT/EP2007/053449, date of mailing Aug. 29, 2007.
PCT counterpart to U.S. Appl. No. 12/376,680, International Search Report and Written Opinion, PCT/EP2007/058132, date of mailing Feb. 6, 2008.
PCT counterpart to U.S. Appl. No. 13/132,821, International Search Report and Written Opinion, PCT/EP2009/066796, date of mailing Jan. 25, 2010.

(Continued)

Primary Examiner — John Pak
Assistant Examiner — Nathan W Schlientz

(57) ABSTRACT

The present invention relates to the use of combinations of 4-bromo-2-(4-chloro-phenyl)-5-(trifluoromethyl)-1H-pyrrole-3-carbonitrile and an oxidizing agent, for eradicating, eliminating or reducing aquatic organisms in ballast water or bilge water whereby 4-bromo-2-(4-chloro-phenyl)-5-(trifluoromethyl)-1H-pyrrole-3-carbonitrile and the oxidizing agent are in respective proportions to provide a synergistic effect against fouling organisms. Suitable oxidizing agents are e.g. bromine, chlorine, ozone, sodium hypochlorite, chlorine dioxide, hydrogen peroxide, potassium permanganate, potassium ferrate, peroxydisulfates such as ammonium peroxydisulfate, sodium peroxydisulfate, and potassium peroxydisulfate; peroxymonocarbonates such as calcium peroxycarbonate and sodium peroxycarbonate; peroxydicarbonates such as sodium peroxydicarbonate and potassium peroxydicarbonate; superoxides such as potassium superoxide and sodium superoxide; peroxides such as potassium peroxide, and sodium peroxide; and Fremy's salts such as potassium nitrosodisulfonate, sodium nitrosodisulfonate, and disodium nitrosodisulfonate.

13 Claims, No Drawings

OTHER PUBLICATIONS

Kull et al., "Mixtures of Quaternary Ammonium Compounds and Long-chain Fatty Acids as Antifungal Agents.", Applied Microbiology, 1961, vol. 9, pp. 538-541.

Limpel et al., "Weed control by dimethyl tetrachloroterephthalate alone and in certain combinations." Proc. Northeast Weed Control Conf., 1962, pp. 48-53, vol. 16.

Colby et al., "Calculating Synergistic and Antagonistic Responses of Herbicide Combinations.", Weeds, Jan. 1967, pp. 20-22, vol. 15(1), Weed Science Society of America.

Richer, D.L., "Synergism—a patent view.", Pestic Sci. 1987, pp. 309-315, vol. 19(4).

Copper Development Association, CDA Technical Note TN11, 1972, pp. 1-22.

Del Amo, B., et al: "A multipurpose compound for protective coatings", Colloids and Surfaces. A, Physicachemical and Engineering Aspects, Elsevier, Amsterdam, NL, vol. 324, No. 1-3, Jul. 1, 2008, pp. 58-64, XP022735387, ISSN: 0927-7757.

International Search Report and Written Opinion, PCT/EP2011/060873, date of mailing Jul. 23, 2012, 13 pages.

* cited by examiner

COMBINATIONS OF 4 BROMO-2-(4-CHLOROPHENYL)-5-(TRIFLUOROMETHYL)-1H-PYRROLE-3-CARBONITRILE AND OXIDIZING AGENTS

CROSS REFERENCE TO RELATED APPLICATIONS

This application is the national stage of Application No. PCT/EP2007/058132, filed Aug. 6, 2007 (hereby incorporated by reference herein), which application claims priority from EP Patent Application No. 06118511.2, filed Aug. 7, 2006.

The present invention relates to the use of combinations of 4-bromo-2-(4-chloro-phenyl)-5-(trifluoromethyl)-1H-pyrrole-3-carbonitrile and an oxidizing agent, for eradicating, eliminating or reducing aquatic organisms in ballast water or bilge water whereby 4-bromo-2-(4-chloro-phenyl)-5-(trifluoromethyl)-1H-pyrrole-3-carbonitrile and the oxidizing agent are in respective proportions to provide a synergistic effect against fouling organisms. Suitable oxidizing agents are e.g. bromine, chlorine, ozone, sodium hypochlorite, chlorine dioxide, hydrogen peroxide, potassium permanganate, potassium ferrate, peroxydisulfates such as ammonium peroxydisulfate, sodium peroxydisulfate, and potassium peroxydisulfate; peroxymonocarbonates such as calcium peroxycarbonate and sodium peroxycarbonate; peroxydicarbonates such as sodium peroxydicarbonate and potassium peroxydicarbonate; superoxides such as potassium superoxide and sodium superoxide; peroxides such as potassium peroxide, and sodium peroxide; and Fremy's salts such as potassium nitrosodisulfonate, sodium nitrosodisulfonate, and disodium nitrosodisulfonate.

The shipping industry is vital to the global marketplace, transporting cargo to and from all corners of the world. In addition to valuable cargo, however, ships may transport thousands of organisms in their ballast water. Ships pump ballast water into the bilge of the ship to provide stability and manoeuvrability during a voyage. Water is taken on at one port when cargo is unloaded and usually discharged at another port when the ship receives cargo. When ballast water is discharged in a remote port the concomitant introduction of non-indigenous organisms has the potential to shift the ecological balance of the local marine ecosystems. Governments and industry are moving to treat ballast water to prevent such undesired marine life exchange. Disinfection of ballast water presents unique challenges to conventional disinfection technologies owing to the large number density of organisms, the diversity of their composition, and the chemical and physical characteristics of ballast water. Ballast water treatment methods are typically categorized as either tanker-based or shore-based treatment technologies. Tanker-based treatment technologies comprise filtration, hydrocyclone treatment, ultra violet irradiation, thermal treatment, and the use of chemicals such as ozone, chlorine, hydrogen peroxide, and biocidal compounds.

Biocidal compounds for use in ballast water treatment should be effective in killing a broad range of marine life forms, have a quick decay rate, and degrade to non-toxic compounds.

4-Bromo-2-(4-chlorophenyl)-5-(trifluoromethyl)-1H-pyrrole-3-carbonitrile is disclosed in EP-0,312,723 for controlling molluscs. Said compound can be represented by the formula:

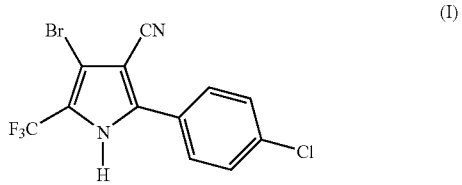 [SMILES: N#Cc1c(-c2ccc(Cl)cc2)[nH]c(C(F)(F)F)c1Br]

(I)

EP-0,746,979 describes the use of 4-bromo-2-(4-chlorophenyl)-5-(trifluoro-methyl)-1H-pyrrole-3-carbonitrile in antifoulant compositions which are applied to underwater surfaces in order to prevent the attachment of fouling organisms to said underwater surfaces.

4-Bromo-2-(4-chlorophenyl)-5-(trifluoromethyl)-1H-pyrrole-3-carbonitrile has a half-life of a few hours at a pH of 8.3 which is the pH of sea water before it degrades into non-toxic compounds. Its half-life increases to a couple of days at neutral and acidic pH.

It has now been found that a combination of 4-bromo-2-(4-chlorophenyl)-5-(trifluoromethyl)-1H-pyrrole-3-carbonitrile (often referred to as component (I)), or a salt thereof, together with one or more oxidizing agents (II) selected from bromine, chlorine, ozone, sodium hypochlorite, chlorine dioxide, hydrogen peroxide, potassium permanganate, potassium ferrate, ammonium peroxydisulfate, sodium peroxydisulfate, potassium peroxydisulfate, calcium peroxycarbonate, sodium peroxycarbonate, sodium peroxydicarbonate, potassium peroxydicarbonate, potassium superoxide, sodium superoxide, potassium peroxide, sodium peroxide, potassium nitrosodisulfonate, sodium nitrosodisulfonate, and disodium nitrosodisulfonate; whereby said component (I) and the oxidizing agent (II) are combined in certain ratios, has a synergistic effect on the control of fouling organisms. As used herein, "control" is defined to include the inhibition of attachment or settlement of fouling organisms to the surface of an object, the removal of fouling organisms that are attached to the surface of an object, and the growth of fouling organisms.

The present invention provides the use of a combination of 4-bromo-2-(4-chlorophenyl)-5-(trifluoromethyl)-1H-pyrrole-3-carbonitrile, or a salt thereof, as a component (I) together with an oxidizing agent (II) selected from bromine, chlorine, ozone, sodium hypochlorite, chlorine dioxide, hydrogen peroxide, potassium permanganate, potassium ferrate, ammonium peroxydisulfate, sodium peroxydisulfate, potassium peroxydisulfate, calcium peroxycarbonate, sodium peroxycarbonate, sodium peroxydicarbonate, potassium peroxydicarbonate, potassium superoxide, sodium superoxide, potassium peroxide, sodium peroxide, potassium nitrosodisulfonate, sodium nitrosodisulfonate, and disodium nitrosodisulfonate; whereby component (I) and the oxidizing agent (II) are in respective proportions to provide a synergistic effect against fouling organisms, for eliminating aquatic organisms in ballast water.

Wherever the term "4-bromo-2-(4-chlorophenyl)-5-(trifluoromethyl)-1H-pyrrole-3-carbonitrile" or component (I) is used throughout this text, it is meant to include said compound both in base or in salt form, the latter being obtained by reaction of the base form with an appropriate acid. Appropriate acids comprise, for example, inorganic acids, such as the hydrohalic acids, i.e. hydrofluoric, hydrochloric, hydrobromic and hydroiodic, sulfuric acid, nitric acid, phosphoric acid, phosphinic acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methyl-benzenesulfonic, cyclohexanesulfamic, 2-hydroxybenzoic, 4-amino-2-hydroxybenzoic and the like acids. Said component (I) may also exist in the form of solvates, such as hydrates.

The ballast water to be disinfected using the combinations of the present invention includes fresh water, sea water and brackish water.

The combinations of the present invention can be used for disinfecting ballast water in tanker-based ballast water treatment systems or in a shore-based ballast water treatment systems.

The aquatic organisms that are commonly found in ballast water comprise phytoplankton (dinoflagellates and diatoms), crustaceans (crabs, shrimp, copepods, amphipods), rotifers, polychaetes, mollusks, fish, echinoderms, ctenophores, coelenterates, bacteria and viruses.

The combination of component (I) and an oxidizing agent (II) can be applied in the form of a composition wherein both said active ingredients are intimately admixed in order to ensure simultaneous administration to the materials to be protected. Application may also be in the form of two separate compositions each comprising respectively component (I) or an oxidizing agent (II) whereby said separate compositions are applied simultaneously in respective proportions to provide a synergistic effect against fouling organisms.

However the combination of component (I) and oxidizing agent (II) can also be a "sequential-combined" administration or application, i.e. component (I) and oxidizing agent (II) are administered or applied alternatively or sequentially in the same place in such a way that they will necessarily become admixed together at the site to be treated. This will be achieved namely if sequential administration or application takes place within a short period of time e.g. within less than 24 hours, preferably less than 15 hours, more preferably less than 3 hours. This alternative method can be carried out for instance by using a suitable single package comprising at least one container filled with a formulation comprising the active component (I) and at least one container filled with a formulation comprising an active component (II).

Component (I), i.e. 4-bromo-2-(4-chlorophenyl)-5-(trifluoromethyl)-1H-pyrrole-3-carbonitrile, may be stored in the form of a concentrated water-dilutable formulation, so that it can easily be stored onboard a ship and used for disinfecting ballast water.

The oxidizing agent (II) may be stored in the form of a solid powder or concentrated water-dilutable formulation, so that it can easily be stored onboard a ship and used for disinfecting ballast water. The oxidizing agent potassium ferrate ($K_2FeO_4$) is a solid that is only stable when kept dry. It decomposes to rust in acidic solution and is only stable in alkaline solution. Ferrates can be conveniently prepared by oxidizing an alkaline solution of an iron(III) salt with concentrated chlorine bleach. Oxidizing agents (II) that are gaseous such as chlorine, chlorine dioxide or ozone may be stored in pressure cylinders or generated on-site and used immediately in the ballast water treatment system. On-site generation of chlorine dioxide may be done for example by reducing sodium chlorate in a strong acid solution with a suitable reducing agent (for example, hydrogen peroxide, sulfur dioxide, or hydrochloric acid). Alternatively chlorine dioxide can also be produced by electrolysis of an aqueous sodium chlorite solution.

In ballast water treatment, the amount of component (I) to be added is such that the concentration of said component (I) in the ballast water tank ranges from 0.01 ppm to 1000 ppm, preferably from 1 to 5 ppm. The amount of oxidizing agent (II) which is added is such a proportion that a synergistic effect against fouling organisms is obtained, in particular the ratio between component (I) and oxidizing agent (II) ranges from 20/80 to 1/99, more particular from 20/80 to 2.5/97.5, even more particular from 20/80 to 5/95.

Suitable formulations for use in the method of the invention can be water-dilutable liquid formulations which can be in the form of an emulsifiable concentrate (EC), a microemulsifiable concentrate (MEC) or a suspension concentrate (SC) containing a high proportion of the active ingredient 4-bromo-2-(4-chloro-phenyl)-5-(trifluoromethyl)-1H-pyrrole-3-carbonitrile. An EC/MEC is a homogeneous liquid composition, usually containing the active ingredient dissolved in a substantially non-volatile and water-immiscible organic solvent. An SC is a fine particle size dispersion of solid active ingredient in water. The concentrated formulations may contain 1 to 80% by weight of 4-bromo-2-(4-chloro-phenyl)-5-(trifluoromethyl)-1H-pyrrole-3-carbonitrile.

The formulations for use in the method of the invention may also be in the form of a solid formulation for dispersion into water such as wettable powder (WP), water dispersible granules (WG) or water dispersible tablets (WT).

Suitable carriers for solid formulations, such as dusts, dispersable or flowable powders, are any dispersant that does not adversely affect the active ingredients, for example, clays (for example, kaolin, bentonite, acid clay, and the like), talcs (for example, talc powder, agalmatolite powder, and the like), silicas (for example, diatomaceous earth, silicic acid anhydride, mica powder, and the like), alumina, sulfur powder, activated charcoal, and the like.

Suitable solvents for the liquid formulations comprising 4-bromo-2-(4-chloro-phenyl)-5-(trifluoromethyl)-1H-pyrrole-3-carbonitrile include methyl ketone, methyl isobutyl ketone, cyclohexanone, xylenes, toluene, chlorobenzene, paraffins, kerosene, white oil, alcohols (e.g. butanol), methylnaphthalene, trimethylbenzene, trichloroethylene, N-methyl-2-pyrrolidone, and tetrahydrofurfuryl alcohol (THFA).

The formulations for use in the method of the invention may further comprise suitable substances known in the art of formulation, such as, for example natural or regenerated mineral substances, solvents, dispersants, surfactants, wetting agents, binders, anti-freeze agents, anti-foaming agents, buffering agents, acidulants, alkalizing substances, corrosion inhibitors, water-repelling agents and other active ingredients. Suitable surfactants are non-ionic, cationic and/or anionic surfactants having good emulsifying, dispersing and wetting properties.

In a further embodiment, the combinations of the present invention are used for disinfecting ballast water treatment in combination with an existing method for ballast water treatment such as filtration, hydrocyclone treatment, ultra violet irradiation, and thermal treatment.

COMPOSITION EXAMPLES

Example 1

Liquid Composition (all Percentages in % w/w)

| | |
|---|---|
| component (I) | 10% |
| Soprophor 796/P ® | 15% |

| | |
|---|---|
| ethoxylated castor oil | 24% |
| acetophenone | as solvent up to 100% |

Soprophor 796/P® is a alpha-[2,4,6-tris[1-(phenyl)ethyl]phenyl]-omega-hydroxy poly(olyethelene)poly(oxypropylene) copolymer comprising from 2 to 8 moles of poly(oxypropylene) units and 16-30 units of poly(oxyethylene) units marketed by Rhodia. Ethoxylated castor oils are available as Alkamuls® from Rhodia, for example, Alkamuls BR®, Alkamuls EL 620 LI®, Alkamuls OR 10®, Alkamuls OR 36®, and Alkamuls OR 40®. A particular group of these ethoxylated castor oils are ethoxylated castor oils containing 12-40 ethoxy units.

The solvent acetophenone can be replaced by other suitable solvents such as benzyl alcohol, butyl lactate, dipropylene glycol n-butyl ether or methyl n-amyl ketone.

Other surfactants for use in these formulations are ethoxylated fatty alcohol, ethoxylated fatty acid and etho-propoxylated block copolymer.

Biological Experiments

Experiment 1

Poison Plate Assay

| | |
|---|---|
| Name of the primary compound: | 4-bromo-2-(4-chloro-phenyl)-5-(trifluoromethyl)-1H-pyrrole-3-carbonitrile as component (I) |
| Name of the combination partners: | hydrogen peroxide (35%) as component (II-a); sodium hypochlorite (14%) as component (II-b); |
| Stock solution: | 32.000 and 8.000 ppm in DMSO |
| Test combinations: | % product A + % product B |
| | 100 + 0 |
| | 20 + 80 |
| | 15 + 85 |
| | 10 + 90 |
| | 5 + 95 |
| | 2.5 + 97.5 |
| | 0 + 100 |

Concentrations of total single active ingredient in the toxicity tests: a series of concentrations increasing with steps of 1/3: 0.08-0.11-0.15-0.20-0.27-0.35-0.47-0.63-0.84-1.13-1.50-2.00-2.67-3.56-4.75-6.33-8.44-11.25-15.00-20.00-26.70-35.60-47.46-63.28-84.38-112.50-150.00-200.00 ppm.

Concentrations of total active ingredient in the combination tests against *Artemia*: a series of concentrations increasing with steps of 1/3: 0.27-0.36-0.48-0.63-0.84-1.13-1.50-2.00-2.67-3.56-4.75-6.33-8.44-11.25-15.00-20.00 ppm.

Concentrations of total active ingredient in the combination tests against algae: a series of concentrations increasing with steps of 1/3: 3.38-4.51-6.01-8.01-10.68-14.24-18.98-25.31-33.75-45.00-60.00-80.00 ppm.

| | |
|---|---|
| Culture medium: | algae: BG 11 liquid mineral medium |
| | *Artemia salina*: artificial seawater |
| Experimental set up: | 24-well plates |
| Species of algae: | (1): *Chlorella vulgaris* CCAP 211/12 |
| | (2): *Anabaena cylindrica* CCAP 1403/2A |
| | (3): *Chlamydomonas sphagnophila* CCAP 11/36E |
| Species of *Artelmia*: | *Artemia salina* (EG *Artemia* Cysts, Great Salt Lake strain) |
| Inoculum: | algae: 1990 µl of a 1/10 dilution in BG 11 of a two week old culture |
| | *Artemia*: 1990 µl artificial seawater with 20-40 *Artemia* larvae (24 hours old) |
| Culture conditions: | 21° C., 65% relative humidity, 1000 lux, 16 hour photoperiod |
| Evaluation: | algae: after 3 weeks of exposure |
| | *Artemia*: after 24 hours of exposure |

Synergism between component (I) and one of the components (II) was determined by a commonly used and accepted method described by Kull F. C. et al. in *Applied Microbiology*, 9, 538-541 (1961) using the Synergy Index, which is calculated as follows for two compounds A and B:

$$\text{Synergy Index } (SI) = \frac{Q_a}{Q_A} + \frac{Q_b}{Q_B}$$

wherein:
$Q_A$ is the concentration of compound A in ppm, acting alone, which produced an end point (e.g. MIC),
$Q_a$ is the concentration of compound A in ppm, in the mixture, which produced an end point (e.g. MIC),
$Q_B$ is the concentration of compound B in ppm, acting alone, which produced an end point (e.g. MIC),
$Q_b$ is the concentration of compound B in ppm, in the mixture, which produced an end point (e.g. MIC).

MIC is the minimum inhibitory concentration, i.e. the lowest concentration of each test compound or mixture of test compounds sufficient to inhibit visible growth.

When the Synergy Index is greater than 1.0, antagonism is indicated. When the SI is equal to 1.0, additivity is indicated. When the SI is less than 1.0, synergism is demonstrated.

When the Synergy Index is greater than 1.0, antagonism is indicated. When the SI is equal to 1.0, additivity is indicated. When the SI is less than 1.0, synergism is demonstrated.

TABLE 1

MIC-values (minimum inhibitory concentration in ppm) and synergy index of various active ingredients and their combination against algae

| Combination | algae species | ratio (I) to (II) | MIC-values in ppm | synergy index |
|---|---|---|---|---|
| (I) + (II-a) | (2) | 100 + 0 | 107.0 | — |
| (I) + (II-a) | (2) | 20 + 80 | 14.2 | 0.48 |
| (I) + (II-a) | (2) | 15 + 85 | 19.0 | 0.66 |
| (I) + (II-a) | (2) | 10 + 90 | 19.0 | 0.69 |
| (I) + (II-a) | (2) | 5 + 95 | 25.3 | 0.96 |
| (I) + (II-a) | (2) | 2.5 + 97.5 | 25.3 | 0.98 |
| (I) + (II-a) | (2) | 0 + 100 | 25.3 | — |
| (I) + (II-a) | (3) | 100 + 0 | 107.0 | — |
| (I) + (II-a) | (3) | 20 + 80 | 45.0 | 0.88 |
| (I) + (II-a) | (3) | 15 + 85 | 45.0 | 0.91 |
| (I) + (II-a) | (3) | 10 + 90 | 45.0 | 0.94 |
| (I) + (II-a) | (3) | 5 + 95 | 33.8 | 0.73 |
| (I) + (II-a) | (3) | 2.5 + 97.5 | 33.8 | 0.74 |
| (I) + (II-a) | (3) | 0 + 100 | 45.0 | — |
| (I) + (II-b) | (2) | 100 + 0 | 107.0 | — |
| (I) + (II-b) | (2) | 20 + 80 | 19.0 | 0.49 |
| (I) + (II-b) | (2) | 15 + 85 | 19.0 | 0.50 |
| (I) + (II-b) | (2) | 10 + 90 | 19.0 | 0.52 |
| (I) + (II-b) | (2) | 5 + 95 | 14.2 | 0.41 |
| (I) + (II-b) | (2) | 2.5 + 97.5 | 19.0 | 0.55 |
| (I) + (II-b) | (2) | 0 + 100 | 33.8 | — |
| (I) + (II-b) | (3) | 100 + 0 | 107.0 | — |

TABLE 1-continued

MIC-values (minimum inhibitory concentration in ppm)
and synergy index of various active ingredients and
their combination against algae

| Combination | algae species | ratio (I) to (II) | MIC-values in ppm | synergy index |
|---|---|---|---|---|
| (I) + (II-b) | (3) | 20 + 80 | 45.0 | 0.42 |
| (I) + (II-b) | (3) | 15 + 85 | 45.0 | 0.42 |
| (I) + (II-b) | (3) | 10 + 90 | 45.0 | 0.42 |
| (I) + (II-b) | (3) | 5 + 95 | 45.0 | 0.42 |
| (I) + (II-b) | (3) | 2.5 + 97.5 | 33.8 | 0.32 |
| (I) + (II-b) | (3) | 0 + 100 | 107.0 | — |

TABLE 2

MIC-values (minimum inhibitory concentration in ppm)
and synergy index of various active ingredients and
their combination against *Artemia salina*

| Combination | ratio (I) to (II) | MIC-values in ppm | synergy index |
|---|---|---|---|
| (I) + (II-b) | 100 + 0 | 0.13 | — |
| (I) + (II-b) | 20 + 80 | 0.48 | 0.74 |
| (I) + (II-b) | 15 + 85 | 0.63 | 0.73 |
| (I) + (II-b) | 10 + 90 | 0.84 | 0.62 |
| (I) + (II-b) | 5 + 95 | 2.00 | 0.78 |
| (I) + (II-b) | 2.5 + 97.5 | 6.33 | 1.25 |
| (I) + (II-b) | 0 + 100 | 200.00 | — |

Experiment 2

Poison Plate Assay

| | |
|---|---|
| Name of the primary compound: | 4-bromo-2-(4-chloro-phenyl)-5-(trifluoromethyl)-1H-pyrrole-3-carbonitrile as component (I) |
| Name of the combination partners: | chlorine dioxide as component (II-c); potassium peroxydisulfate as component (II-d); potassium superoxide as component (II-e); potassium peroxide as component (II-f); potassium nitrosodisulfonate as component (II-g); potassium (VI) ferrate as component (II-h); |
| Stock solution: | 32.000 and 2500 ppm in DMSO |
| Test combinations: | % product A + % product B |
| | 100 + 0 |
| | 20 + 80 |
| | 15 + 85 |
| | 10 + 90 |
| | 5 + 95 |
| | 2.5 + 97.5 |
| | 0 + 100 |

Concentrations of total active ingredient in the combination tests against algae: a series of concentrations increasing with steps of 1/3: 3.38-4.51-6.01-8.01-10.68-14.24-18.98-25.31-33.75-45.00-60.00-80.00 ppm.

| | |
|---|---|
| Culture medium: | algae: BG 11 liquid mineral medium |
| Experimental set up: | 24-well plates |
| Species of algae: | (1): *Chlorella vulgaris*  CCAP 211/12 |
| | (2): *Anabaena cylindrica*  CCAP 1403/2A |
| | (3): *Chlamydomonas sphagnophila*  CCAP 11/36E |
| | (4): *Tribonema* sp.  CCAP 880/2 |
| Inoculum: | algae: 1990 µl of a 1/10 dilution in BG 11 of a two week old culture |
| Culture conditions: | 21° C., 65% relative humidity, 1000 lux, 16 hour photoperiod |
| Evaluation: | algae: after 3 weeks of exposure |

Synergism between component (I) and one of the components (II) was determined using the Synergy Index as outlined above in Experiment 1.

TABLE 3

MIC-values (minimum inhibitory concentration in ppm)
and synergy index of various active ingredients
and their combination against algae

| Combination | algae species | ratio (I) to (II) | MIC-values in ppm | synergy index |
|---|---|---|---|---|
| (I) + (II-c) | (1) | 100 + 0 | 107.0 | — |
| (I) + (II-c) | (1) | 20 + 80 | 9.49 | 0.82 |
| (I) + (II-c) | (1) | 15 + 85 | 7.12 | 0.65 |
| (I) + (II-c) | (1) | 10 + 90 | 7.12 | 0.68 |
| (I) + (II-c) | (1) | 5 + 95 | 9.49 | 0.95 |
| (I) + (II-c) | (1) | 2.5 + 97.5 | 9.49 | 0.98 |
| (I) + (II-c) | (1) | 0 + 100 | 9.49 | — |
| (I) + (II-d) | (1) | 100 + 0 | 107.0 | — |
| (I) + (II-d) | (1) | 20 + 80 | 45.0 | 0.68 |
| (I) + (II-d) | (1) | 15 + 85 | 45.0 | 0.70 |
| (I) + (II-d) | (1) | 10 + 90 | 45.0 | 0.72 |
| (I) + (II-d) | (1) | 5 + 95 | 45.0 | 0.73 |
| (I) + (II-d) | (1) | 2.5 + 97.5 | 45.0 | 0.74 |
| (I) + (II-d) | (1) | 0 + 100 | 60.0 | — |
| (I) + (II-e) | (2) | 100 + 0 | 19 | — |
| (I) + (II-e) | (2) | 20 + 80 | 25.3 | 0.72 |
| (I) + (II-e) | (2) | 15 + 85 | 25.3 | 0.68 |
| (I) + (II-e) | (2) | 10 + 90 | 25.3 | 0.64 |
| (I) + (II-e) | (2) | 5 + 95 | 25.3 | 0.60 |
| (I) + (II-e) | (2) | 2.5 + 97.5 | 25.3 | 0.58 |
| (I) + (II-e) | (2) | 0 + 100 | 45.0 | — |
| (I) + (II-f) | (2) | 100 + 0 | 25.3 | — |
| (I) + (II-f) | (2) | 20 + 80 | 10.7 | 0.88 |
| (I) + (II-f) | (2) | 15 + 85 | 10.7 | 0.91 |
| (I) + (II-f) | (2) | 10 + 90 | 10.7 | 0.94 |
| (I) + (II-f) | (2) | 5 + 95 | 10.7 | 0.97 |
| (I) + (II-f) | (2) | 2.5 + 97.5 | 10.7 | 0.99 |
| (I) + (II-f) | (2) | 0 + 100 | 10.7 | — |
| (I) + (II-g) | (2) | 100 + 0 | 6.00 | — |
| (I) + (II-g) | (2) | 20 + 80 | 14.2 | 0.62 |
| (I) + (II-g) | (2) | 15 + 85 | 14.2 | 0.51 |
| (I) + (II-g) | (2) | 10 + 90 | 33.8 | 0.94 |
| (I) + (II-g) | (2) | 5 + 95 | 45.0 | 0.91 |
| (I) + (II-g) | (2) | 2.5 + 97.5 | 45.0 | 0.74 |
| (I) + (II-g) | (2) | 0 + 100 | 80.0 | — |
| (I) + (II-h) | (4) | 100 + 0 | 107.0 | — |
| (I) + (II-h) | (4) | 20 + 80 | 80.0 | 0.95 |
| (I) + (II-h) | (4) | 15 + 85 | 80.0 | 0.96 |
| (I) + (II-h) | (4) | 10 + 90 | 80.0 | 0.97 |
| (I) + (II-h) | (4) | 5 + 95 | 80.0 | 0.99 |
| (I) + (II-h) | (4) | 2.5 + 97.5 | 80.0 | 0.99 |
| (I) + (II-h) | (4) | 0 + 100 | 80.0 | — |

The invention claimed is:
1. A combination of 4-bromo-2-(4-chlorophenyl)-5-(trifluoromethyl)-1H-pyrrole-3-carbonitrile, or a salt thereof, as a component (I) together with an oxidizing agent (II) selected from the group consisting of sodium hypochlorite, chlorine dioxide, hydrogen peroxide, potassium ferrate, potassium peroxydisulfate, potassium superoxide, potassium peroxide, and potassium nitrosodisulfonate;

whereby component (I) and the oxidizing agent (II) are in respective proportions to provide a synergistic effect against fouling organisms.

2. A combination according to claim 1 wherein the oxidizing agent is chlorine dioxide.

3. A combination according to claim 1 wherein the oxidizing agent is potassium ferrate.

4. A combination according to claim 1 wherein the oxidizing agent is hydrogen peroxide or sodium hypochlorite.

5. A combination according to claim 1 wherein the ratio of component (I) to the oxidizing agent (II) ranges from 20/80 to 1/99.

6. A combination according to claim 5 wherein the ratio of component (I) to the oxidizing agent (II) ranges from 20/80 to 5/95.

7. A combination according to claim 1 wherein the amount of component (I) ranges from 0.01 ppm to 1000 ppm.

8. A method for eliminating aquatic organisms in ballast water comprising applying to underwater surfaces a combination of 4-bromo-2-(4-chlorophenyl)-5-(trifluoromethyl)-1H-pyrrole-3-carbonitrile, or a salt thereof, as a component (I) together with an oxidizing agent selected from the group consisting of sodium hypochlorite, chlorine dioxide, hydrogen peroxide, potassium ferrate, potassium peroxydisulfate, potassium superoxide, potassium peroxide, and potassium nitrosodisulfonate; whereby component (I) and the oxidizing agent (II) are in respective proportions to provide a synergistic effect against fouling organisms.

9. The method according to claim 8 wherein the ratio of component (I) to the oxidizing agent (II) ranges from 20/80 to 1/99.

10. The method according to claim 8 wherein component (I) and the oxidizing agent (II) are applied in the form of a composition comprising component (I) and the oxidizing agent (II).

11. The method according to claim 8 wherein component (I) and the oxidizing agent (II) are applied in the form of a two separate compositions comprising respectively component (I) and the oxidizing agent (II) whereby said two compositions are applied simultaneously.

12. The method according to claim 8 wherein component (I) and the oxidizing agent (II) are applied in the form of a two separate compositions comprising respectively component (I) and the oxidizing agent (II) whereby said two compositions are applied sequentially.

13. The method according to claim 8 in combination with a method for treating ballast water selected from the group consisting of filtration, hydrocyclone treatment, ultra violet irradiation, and thermal treatment.

* * * * *

UNITED STATES PATENT AND TRADEMARK OFFICE
CERTIFICATE OF CORRECTION

PATENT NO. : 8,399,506 B2  Page 1 of 1
APPLICATION NO. : 12/376680
DATED : March 19, 2013
INVENTOR(S) : Tony Mathilde Jozef Kempen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 801 days.

Signed and Sealed this
First Day of September, 2015

Michelle K. Lee
*Director of the United States Patent and Trademark Office*